United States Patent [19]
Slaugh et al.

[11] Patent Number: 6,018,089
[45] Date of Patent: Jan. 25, 2000

[54] PROCESS FOR SEPARATING LINEAR INTERNAL OLEFINS FROM BRANCHED INTERNAL OLEFINS

[75] Inventors: Lynn Henry Slaugh; Laurent Alain Fenouil, both of Houston; Howard Lam-Ho Fong, Sugar Land, all of Tex.

[73] Assignee: Shell Oil Company, Houston, Tex.

[21] Appl. No.: 08/987,554

[22] Filed: Dec. 9, 1997

[51] Int. Cl.[7] ...................................................... C07C 7/00
[52] U.S. Cl. ........................... 585/867; 585/833; 585/809
[58] Field of Search .................................. 585/809, 833, 585/867, 25, 26, 436

[56] References Cited

U.S. PATENT DOCUMENTS

| | | | |
|---|---|---|---|
| 2,775,633 | 12/1956 | Fenske et al. | 585/809 |
| 2,953,611 | 9/1960 | Spengler | 585/809 |
| 3,306,946 | 2/1967 | Snyder et al. | 585/809 |
| 3,444,261 | 5/1969 | Caprioli et al. | 585/809 |
| 3,534,116 | 10/1970 | Fuller | 585/867 |
| 3,864,420 | 2/1975 | Dombro | 585/664 |
| 4,710,273 | 12/1987 | Okamoto | 203/29 |
| 4,915,794 | 4/1990 | Slaugh et al. | 203/29 |
| 4,946,560 | 8/1990 | Slaugh et al. | 203/38 |
| 5,012,034 | 4/1991 | Weingaertner et al. | 585/806 |

OTHER PUBLICATIONS

U.S. application No. 08/987,553, Slaugh et al., filed Dec. 9, 1997.
U.S. application No. 08/876,822, Slaugh et al., filed Jun. 16, 1997.

*Primary Examiner*—Walter D. Griffin
*Attorney, Agent, or Firm*—Dennis V. Carmen

[57] ABSTRACT

A feedstock of linear internal olefins and branched internal olefins are converted to a primarily linear internal olefin composition having a lower concentration of branched internal olefins than present in the feedstock, by:

a) contracting the feedstock with linear polyaromatic compound under conditions effective to form a reaction mixture comprising an linear polyaromatic compound-linear internal olefin adduct;

b) separating the linear polyaromatic compound-linear internal olefin adduct from the reaction mixture;

c) dissociating the linear polyaromatic compound-linear internal olefin adduct to form linear polyaromatic compound and a linear internal olefin composition, and d) separating the linear polyaromatic compound formed in step c) from a linear internal olefin composition.

21 Claims, No Drawings

PROCESS FOR SEPARATING LINEAR INTERNAL OLEFINS FROM BRANCHED INTERNAL OLEFINS

1. FIELD OF THE INVENTION

This invention relates to a process for separating linear internal olefins from branched internal olefins.

2. BACKGROUND OF THE INVENTION

Many industrial processes produce olefins that are mixtures of linear internal olefins and branched alpha olefins. Olefins are frequently used in the manufacture of polymers or as drilling mud additives, or as intermediates for the production of oil additives and detergents. Depending upon the particular application, it would be desirable to manufacture a linear internal olefin composition having the greatest purity possible. For example, detergents manufactured from linear internal olefins are more biodegradable than detergents derived from many industrially manufactured olefin streams containing branched internal olefins. While pure species of linear internal olefins with a narrow carbon number range can be manufactured or produced in small quantities at a great cost, we have found that it would be particularly desirable to economically provide large quantities of a purified linear internal olefins from raw feedstocks containing a mixture of linear internal olefins and branched internal olefins.

Separating and isolating linear internal olefins from branched internal olefins is no easy task, especially when these species have similar or identical molecular weights or carbon numbers. Conventional distillation methods are inadequate to separate species of this type which have such closely related boiling points. The separation problem is further aggravated in that the linear internal olefin species not only needs to be separated from branched internal olefins, but also from everything else present in the feedstock mixture, such as saturated hydrocarbons. U.S. Pat. No. 4,946,560 described a process for the separation of internal olefins from alpha olefins by contacting a feedstock with anthracene to form an olefin adduct, separating the adduct from the feedstock, dissociating the anthracene-linear alpha olefin adduct through heat to produce anthracene and an olefin composition enriched in alpha olefin, and separating out the anthracene from the alpha olefin. We have found it desirable, however, to produce an olefin stream which is rich in linear internal olefins.

3. SUMMARY OF THE INVENTION

This invention relates to a process for separating linear internal olefins from branched internal olefins. In particular, there is provided a process for converting a feedstock, comprising linear internal olefins and branched internal olefins to a linear internal olefin composition having a lower concentration of branched internal olefins than present in the feedstock, comprising:

a) contacting the feedstock with a linear polyaromatic compound under conditions effective to form a reaction mixture comprising a linear polyaromatic compound-linear internal olefin adduct;

b) separating the linear polyaromatic compound-linear internal olefin adduct, and optionally the unreacted linear polyaromatic compound as well, from the reaction mixture;

c) dissociating the linear polyaromatic compound-linear internal olefin adduct to form a linear polyaromatic compound and a linear internal olefin composition, and d) separating the linear polyaromatic compound formed in step c) from a linear internal olefin composition.

4. DETAILED DESCRIPTION OF THE INVENTION

A linear internal olefin(s) is an olefin whose double bond in located anywhere along the carbon chain except at a terminal carbon atom. The linear internal olefin does not have any alkyl, aryl, or alicyclic branching on any of the double bond carbon atoms or on any carbon atoms adjacent to the double bond carbon atoms.

A branched internal olefin(s) is an olefin whose double bond in located anywhere along the carbon chain except at a terminal carbon atom. The branched internal olefin has one or more alkyl, aryl, or alicyclic branches on one or more double bond carbon atoms or on any carbon atom adjacent to a double bond carbon atom.

The feedstock olefins used in the process of the invention comprise linear internal olefins and branched internal olefins. The feedstock may optionally contain other kinds of olefins, aromatic compounds, paraffins, and oxygenated compounds. The feedstock is generally produced by commercial processes such as the oligomerization of ethylene, followed by isomerization and disproportionation. Alternatively, the feedstock may be produced by the Fisher-Tropsch process, which may contain some branched species. Another process for making internal olefins is to dimerize or oligomerize propylene and higher olefins using conventional organo-metallic dimerization catalysts or molecular sieves such as ZSM zeolites or SAPO.

The amount of branched internal olefins, linear internal olefins, and other optional ingredients present in the feedstock is not particularly limited. In fact, the feedstock may contain as little as 5 wt. % of internal olefins and up to 95% of internal olefins, based on the weight of all ingredients in the feedstock. However, the process of the invention is particularly suited to an industrial scale production of a linear internal olefin stream. Accordingly, in a preferred embodiment of the invention, the feedstock to be treated according to the process of the invention contains at least 50 wt. % of internal olefins and up to 95 wt. % of internal olefins.

Generally, the feedstock will contain from 5 wt. % to 90 wt. % of linear internal olefins, but preferably from 25 wt % to 80 wt. % of linear internal olefins, based on the weight of all ingredients in the feedstock. The particular amount will often vary with the method of manufacturing the feedstock, such as by oligomerizing olefins or by the Fisher-Tropsch process.

The amount of branched internal olefin in the feedstock is generally in the range of 5 wt. % to 95 wt. % based on the weight of the feedstock stream, with amounts ranging from 20 wt. % to 75 wt. % being more common and more suitable to justify a separation process and yield desired product.

Other ingredients which may be present in the feedstock include alpha olefins, aromatic compounds, paraffins, and oxygenated compounds. Since the linear polyaromatic compound preferentially forms an adduct with alpha olefins, thereby interfering with the formation of a linear polyaromatic compound-linear internal olefin adduct, it is preferred that the feedstream should contain only minor amounts of alpha olefin, such as less than 5 wt. % of alpha olefins, and more preferably 2 wt. % or less, most preferably 0.5 wt. % or less. Besides the alpha olefins, the other ingredients may be present in the feedstock in amounts ranging from 0 wt. % to 50 wt. %, based on the weight of the feedstock.

Typically the feed olefins will have an average carbon number ranging from about 4 to about 22, more preferably from about 6 to about 18. The physical properties demanded by the end use of the olefins in part determines the suitable carbon numbers to be isolated. Olefins with carbon numbers greater than 22 and lower than 6 can be utilized in the instant process, but from a commercially practical point of view, feedstocks with carbon numbers ranging from about 6 to about 18 will be most frequently used as such, as intermediates for derivatives, or oligomerized, for use in the field of detergents, plasticizers, metal working lubricants, and well-bore drilling fluids.

The linear polyaromatic compound is utilized in the instant process to form the adduct with the linear internal olefins in the feed stream. While not being bound to a theory, it is believed that the linear polyaromatic compound preferentially forms an adduct with the linear internal olefins and to a lesser extent with the branched internal olefins. The preferential adduction of linear polyaromatic compound toward the linear internal olefin over the branched internal olefins may be due to the steric hindrance and/or electronic effects of the latter olefins in a Diels-Alder reaction.

As used herein, "linear polyaromatic compound" refers to a linear polyaromatic compound having at least three fused aromatic rings, which may be unsubstituted or substituted and possess similar adducting properties as the unsubstituted molecule, and mixtures thereof The linearity should extend to at all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a hydrocarbon chain, an ether linkage, or a ketone group containing chain; as well as those containing a heteroatom which do not interfere in the separation of the linear internal olefins from the branched internal olefins.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected to that they are relatively inert under the reaction conditions and relatively small to avoid sterically hindering the formation of the Diels-Alder adduct. Suitable substituted linear polyaromatic compounds can be determined by routine experimentation. Examples of suitable linear polyaromatic compounds include 9,10-dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene.

The process of the instant invention is basically a three step process wherein (a) linear polyaromatic compound is reacted with a feedstock containing branched and linear internal olefins to form an adduct, (b) the adduct is separated from the reaction mixture, and (c) the adduct is dissociated to release the olefin and regenerate the linear polyaromatic compound. The Diels-Alder adduct forming reaction is carried out in a conventional fashion and reaction zone. An example of a suitable reaction zone is a continuously stirred tank reactor wherein olefin and linear polyaromatic compound are added continuously to a stirred tank, and the reaction mixture is continuous withdrawn from the stirred tank. Alternatively, the reaction may be carried out in a batch reactor, wherein the olefin and the linear polyaromatic compound are charged to an autoclave which is then heated to a reaction temperature sufficient to complete the reaction. The reaction is typically carried out over a range of temperatures from about 150° to about 290° C., preferably from about 200° to about 280° C., and most preferably from about 240° to about 265° C. Pressures are not critical and typically run from about atmospheric to about 100 atmospheres. The reaction can be carried out in the gas phase under vacuum or liquid phase or mixed gas-liquid phase, depending on the volatility of the feed olefins, but generally in the liquid phase.

Stoichiometric proportions or an excess of either olefin or linear polyaromatic compound can be used in forming the adducts, but a molar excess of olefin is preferred. The molar ratio of olefin to linear polyaromatic compound is preferably from greater than 0.5:1 up to 10:1, more preferably from 1.5:1 to 7:1.

An inert solvent can be utilized to dissolve the feed olefins or the linear polyaromatic compound or both in the reactor. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

In one embodiment of the invention, however, the feedstock and linear polyaromatic compound-linear internal olefin adduct formation is carried out in the absence of a solvent. We have found that the absence of a solvent does not substantially affect the amount of linear polyaromatic compound regenerated under equivalent reaction conditions, and that the concentration of linear internal olefins generated is substantially the same. Thus, in a preferred embodiment, the process of the invention is conducted in the absence of a solvent.

After the linear polyaromatic compound-olefin adduct has been formed, it is separated from the reaction mixture. The olefin-linear polyaromatic compound adduct is separated from the reaction mixture by conventional means. Due to the large molecular weight and structural difference between the linear polyaromatic compound-linear internal olefin adduct and the remainder of the reaction mixture, conventional separation techniques are quite suitable for removing the unreacted olefins from the linear polyaromatic compound-linear internal olefin adduct. For example, the unreacted olefins may be removed at the overhead or in fractions by vacuum or flash distillation of the reaction mixture to leave the linear polyaromatic compound-linear internal olefin adduct and unreacted linear polyaromatic compound as a liquid bottoms. The other unreacted components of the reaction mixture, such as the unreacted olefins as well as paraffins, aromatics, alcohols, ketones, acids, and other impurities may be distilled off. Alternatively, the linear polyaromatic compound-linear internal olefin adduct is separated by cooling the reaction mixture until the adduct crystallizes out, followed by filtration or centrifugation to remove the unreacted olefin. In most cases the unreacted linear polyaromatic compound will separate out with the linear polyaromatic compound-linear internal olefin adduct. The remainder of the reaction mixture can be used in other processes or applications since is will have an enriched internal olefin content over that of the feedstock.

The next step of the instant process is to dissociate the linear polyaromatic compound-linear internal olefin adduct. The dissociation process can be accomplished by heating or pyrolyzing the recovered linear polyaromatic compound-linear internal olefin adduct at a temperature of from about 250° to about 400° C., preferably from about 300° to about 350° C. This pyrolysis frees the linear internal olefins from the linear polyaromatic compound. The linear polyaromatic compound is then separated from the resulting mixture by any conventional means, which may occur simultaneously with the pyrolysis operation, such as by vacuum or flash distilling off the linear internal olefins along with any impurities at the pyrolysis temperatures, and removing the linear polyaromatic compound as a bottoms from the adduct dissociating zone. Other separation techniques include filtration and centrifugation. The linear polyaromatic compound may be recycled back to the adduct reaction zone. The separated linear internal olefin composition is enriched in linear internal olefin content over that of the feedstock, and the concentration of the branched internal olefins in the linear internal olefin composition is reduced over that of the feedstock.

While most of the branched internal olefins will have been separated from the linear internal olefins, a small amount of branched internal olefins, along with other impurities may be present in the final linear internal olefin composition. For many applications, the amount of branched internal olefins in the linear internal olefin composition after one pass through the process of the invention is sufficiently small that only one pass through the process is necessary. If desired, however, the linear internal olefin composition may be subjected to multiple passes through additional reaction zone and adduct dissociating reactors fed by the linear internal olefin composition produced from the prior pass, to further reduce the branched internal olefin content and further enhance the linear internal olefin content. In a preferred embodiment, the process of the invention is repeated more than once, more preferably 2–4 times.

The amount of branched internal olefins in the linear internal olefin composition is less than 3 wt. % after subjecting the feedstock to the process of the invention.

Preferably, the amount of branched internal olefins in the linear internal olefin composition is 2.5 wt. % or less, more preferably 2.0 wt. % or less, most preferably 1.5 wt. % or less. With multiple passes, the content of the branched internal olefins can be reduced in the linear internal olefin composition to 1.0 wt. % or less, more preferably 0.7 wt. % or less, most preferably 0.5 wt. % or less.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention.

The present invention will now be illustrated by means of the following illustrative embodiments and examples which are provided for illustration and are not to be construed as limiting the invention.

EXAMPLE

To illustrate the concept of the invention, several samples of six-carbon atom internal olefins having different compositions were used as the feedstocks. The composition of each feedstock sample is set forth in Table 1 below. 0.054 moles of linear polyaromatic compound was charged to a 100 ml. Parr autoclave, purged three times with nitrogen, and sealed. The autoclave was placed in a dry box and 0.108 moles of a nitrogen purged feedstock sample was added to the autoclave, along with 10 ml. of dry, nitrogen-purged toluene in samples 1 and 2. The autoclave was sealed, removed from the dry box, placed in a heating mantle and heated to 255° C. The reaction time for samples 1 and 2 containing the toluene solvent was about 3 hours. The reaction time for samples 3– 5 without solvent was about 1 hour. The autoclave contents were stirred during heating. Once the reaction was complete, the autoclave was cooled to 20° C. The unreacted, excess olefin feedstock was removed by distillation from the product mixture. The remaining unconverted linear polyaromatic compound and the linear polyaromatic compound-linear internal olefin adduct mixture was then heated to 300–350° C. for about 0.5 hours, during which time the linear polyaromatic compound-linear internal olefin adduct dissociated to recyclable linear polyaromatic compound and the internal olefin composition product enriched in linear internal olefins relative to the moles of internal olefins in the feedstock.

This linear internal olefin composition was analyzed by gas chromatography. The results are shown in Table 1. The concentration of the species within the feedstock and within the resulting linear internal olefin composition are reported as weight percentages.

TABLE 1

SEPARATION OF LINEAR AND BRANCHED INTERNAL OLEFINS

| SAMPLE | COMPOSITION | 2-HEXENE | 3-HEXENE | 2-METHYL-2-PENTENE | 3-METHYL-2-PENTENE | 4-METHYL-2-PENTENE |
|---|---|---|---|---|---|---|
| 1 | Feedstock | 50.4 | — | 49.6 | — | — |
| 1 | Product | 93.5 | — | 6.5 | — | — |
| 2 | Feedstock | 33.2 | 33.0 | 33.8 | — | — |
| 2 | Product | 43.2 | 53.4 | 3.4 | — | — |
| 3 | Feedstock | 51.0 | — | — | 49.0 | — |
| 3 | Product | 93.4 | — | — | 6.6 | — |

TABLE 1-continued

SEPARATION OF LINEAR AND BRANCHED INTERNAL OLEFINS

| SAMPLE | COMPOSITION | 2-HEXENE | 3-HEXENE | 2-METHYL-2-PENTENE | 3-METHYL-2-PENTENE | 4-METHYL-2-PENTENE |
|---|---|---|---|---|---|---|
| 4 | Feedstock | 49.7 | — | — | — | 50.3 |
| 4 | Product | 86.1 | — | — | — | 13.9 |
| 5 | Feedstock | — | 50.0 | — | — | 50.0 |
| 5 | Product | — | 77.9 | — | — | 22.1 |

The results indicate that in each sample, the amount of linear internal olefin was enriched in the product while the amount of branched internal olefin was drastically reduced. In some cases, the amount of branched internal olefin was reduced by more than 80%, even over 90%, over the amount present in the feedstock.

What we claim is:

1. A process for converting a feedstock comprising linear internal olefins and branched internal olefins, to a linear internal olefin composition having a lower mole concentration of branched internal olefins than present in the feedstock, comprising:
   a) contacting the feedstock with linear polyaromatic compound under conditions effective to form a reaction mixture comprising a linear polyaromatic compound-linear internal olefin adduct;
   b) separating the linear polyaromatic compound-linear internal olefin adduct from the reaction mixture;
   c) dissociating the linear polyaromatic compound-linear internal olefin adduct to form linear polyaromatic compound and a linear internal olefin composition, and optionally
   d) separating the linear polyaromatic compound formed in step c) from the linear internal olefin composition.

2. The process of claim 1, wherein the feedstock is contacted with linear polyaromatic compound at a temperature ranging from 150° to about 290° C.

3. The process of claim 2, wherein the feedstock is contacted with linear polyaromatic compound at a temperature ranging from about 220° to about 265° C.

4. The process of claim 1, wherein the molar ratio of olefins in the feedstock to linear polyaromatic compound ranges from greater than 0.5:1 to 7:1.

5. The process of claim 1, wherein the linear polyaromatic compound-linear internal olefin adduct is dissociated by heating the linear polyaromatic compound-linear internal olefin adduct to a temperature ranging from about 250° C. to 400° C.

6. The process of claim 5, wherein the linear polyaromatic compound-linear internal olefin adduct is heated to a temperature ranging from about 300° C. to 350° C.

7. The process of claim 1, wherein the separations are carried out by vacuum or flash distillation.

8. The process of claim 1, wherein the separation in step b) is carried out by first cooling followed by filtration or centrifugation.

9. The process of claim 1, wherein the feedstock comprises 1 wt. % or more of branched internal olefins.

10. The process of claim 1, wherein the feedstock is contacted with the linear polyaromatic compound in the absence of a solvent.

11. The process of claim 1, wherein steps a)–c) are repeated more than once.

12. The process of claim 1, wherein the molar percentage of branched internal olefins in the feedstock based on the total moles of internal olefins in the feedstock is reduced by 50% or more.

13. The process of claim 12, wherein the molar percentage of branched internal olefins in the feedstock based on the total moles of internal olefins in the feedstock is reduced by 70% or more.

14. The process of claim 1, wherein the steps a)–c) are repeated more than once, and the molar weight of the branched internal olefins in the feedstock based on the total moles of internal olefins in the feedstock prior to first contact with linear polyaromatic compound in step a), is reduced by 80% or more.

15. The process of claim 1, wherein the feedstock comprises 5 wt. % to 95 wt. % of linear internal olefins.

16. The process of claim 15, wherein the feedstock comprises 25 wt. % to 80 wt. % of linear internal olefins.

17. The process of claim 1, wherein the average carbon number of the feedstock olefins ranges from 4 to 18.

18. The process of claim 1, wherein the average carbon number of the feedstock olefins ranges from 6 to 18.

19. The process of claim 1, wherein the amount of branched internal olefin in the feedstock is at least 5 wt. %.

20. The process of claim 1, wherein the total amount of internal olefin in the feedstock ranges from 5 wt. % to 95 wt. %.

21. The process of claim 20, wherein the total amount of internal olefin in the feedstock ranges from 50 wt. % to 95 wt. %.

* * * * *